United States Patent
Bastia (10) Patent No.: US 10,463,244 B2
(45) Date of Patent: Nov. 5, 2019

(54) PROCTOSCOPE

(71) Applicant: THD S.P.A., Correggio (Reggio Emilia) (IT)

(72) Inventor: Filippo Bastia, Soliera (IT)

(73) Assignee: THD S.P.A., Correggio (IT)

( * ) Notice: Subject to any disclaimer, the term of this patent is extended or adjusted under 35 U.S.C. 154(b) by 0 days.

(21) Appl. No.: 15/819,715

(22) Filed: Nov. 21, 2017

(65) Prior Publication Data
US 2018/0146849 A1 May 31, 2018

(30) Foreign Application Priority Data

Nov. 30, 2016 (IT) .......................... 102016000121462

(51) Int. Cl.
*A61B 1/31* (2006.01)
*A61B 1/00* (2006.01)
(Continued)

(52) U.S. Cl.
CPC ............. *A61B 1/31* (2013.01); *A61B 1/00128* (2013.01); *A61B 1/00149* (2013.01); *A61B 1/018* (2013.01); *A61B 1/042* (2013.01); *A61B 1/32* (2013.01); *A61M 29/00* (2013.01); *A61M 2210/1067* (2013.01)

(58) Field of Classification Search
CPC ............. A61B 1/31; A61B 1/32; A61M 29/00
See application file for complete search history.

(56) References Cited

U.S. PATENT DOCUMENTS 3,701,347 A * 10/1972 Belkin ..................... A61B 1/31
600/184
6,428,473 B1 8/2002 Leonard et al.
(Continued)

FOREIGN PATENT DOCUMENTS

CN 201153991 * 11/2008
CN 201153991 Y 11/2008
(Continued)

*Primary Examiner* — Julianna N Harvey
(74) *Attorney, Agent, or Firm* — Pearne & Gordon LLP (57) ABSTRACT

A proctoscope, comprising a dilator body (2), having a longitudinal axis of extension (X) and internally hollow so as to define an internal volume (V), and at least one handle (5) applied to said dilator body (2), wherein the dilator body (2) has a distal portion (2a), having a substantially tubular shape and defining a zone of dilation of an internal cavity of a patient, and a proximal portion (2b) extending from the distal portion (2a) in a diverging fashion and defining a rear opening (4) for accessing said internal volume (V), wherein said distal portion (2a) of the dilator body (2) has at least one front opening (3) to enable access to the patient's mucosa or tissue from said internal volume (V), and wherein said diverging proximal portion (2b), or, alternatively, said at least one handle (5), has an anchorage means (6) for an adaptor body (100) suitable for placing a detection device (200) in a position such as to detect the internal volume of the proctoscope (1). Said dilator body (2) has, on said diverging proximal portion (2b), at least one auxiliary access opening (7) configured to enable the insertion of a means for operating in the internal volume (V) through said auxiliary opening (7) in a configuration wherein the proctoscope (1) is associated with said adaptor body (100).

15 Claims, 7 Drawing Sheets

(51) Int. Cl.
*A61B 1/018* (2006.01)
*A61B 1/32* (2006.01)
*A61M 29/00* (2006.01)
*A61B 1/04* (2006.01)

(56) References Cited

U.S. PATENT DOCUMENTS

| | | | |
|---|---|---|---|
| D612,046 S * | 3/2010 | Tsai | D24/135 |
| 2003/0130559 A1* | 7/2003 | Morin | A61B 1/00073 600/104 |
| 2011/0087075 A1* | 4/2011 | Wenchell | A61B 1/00154 600/235 |
| 2012/0016204 A1* | 1/2012 | Bastia | A61B 1/00108 600/245 |
| 2013/0225925 A1* | 8/2013 | Kang | A61B 1/00154 600/114 |

FOREIGN PATENT DOCUMENTS

| | | |
|---|---|---|
| EP | 1929959 A1 | 6/2008 |
| WO | 2010048965 A1 | 5/2010 |

\* cited by examiner

PROCTOSCOPE

The present invention relates to a proctoscope.

The present invention relates more generally to a device for inspecting an internal cavity of a patient, to be understood as a natural cavity, for example an anal and/or vaginal cavity, or an artificial cavity fashioned by a surgeon.

Hereinafter precise reference will be made to the field of coloproctology, i.e. to devices such as anoscopes, proctoscopes or rectoscopes, although the present invention can have other surgical applications.

The use of proctoscopes as instruments for investigating the mucosa of the anal canal of a patient is known. Such instruments generally comprise a hollow dilator body, insertable into the anal canal of the patient and provided with a front opening in order to visually access the mucosa of the anal canal. The dilator body is provided at the rear with a gripping handle and is further provided, on its rear flange, with suitable coupling members for an adaptor body which is configured to support a camera. During use, the camera takes images of the mucosa through the internal cavity of the dilator body and through the front opening.

Proctoscopes of a traditional type are designed for solely diagnostic purposes, i.e. for taking images of the mucosa, and are therefore not compatible with surgical applications that require a surgeon to access the internal cavity of the dilator body. Such access, in proctoscopes of the above-described type, is precluded by the fact that the camera and the adaptor body occlude the rear access opening, preventing the insertion of any type of surgical instrument (for example, an electrosurgical unit).

Therefore, in the event of surgical implications, the surgeon is obliged to remove the camera and the adaptor. Besides complicating the procedure and introducing risks of contaminating the surrounding environment with the patient's fluids (the camera is removed while the proctoscope is still inserted in the patient's anal canal), this precludes documenting the operation by capturing images or videos.

The task of the present invention is thus to provide a proctoscope that is free of the above-mentioned drawbacks.

In particular, it is an object of the invention to provide a proctoscope that has a high flexibility of use.

This object is substantially achieved by a proctoscope having the features set forth in one or more of the appended claims.

A preferred, but not exclusive, embodiment of a proctoscope in accordance with the present invention will now be illustrated by way of non-limiting example.

With reference to the appended figures, 1 denotes a proctoscope in its entirety. The present invention may also be extended in a more general form to a device for inspecting an internal cavity of a patient, without going outside the claimed scope of protection.

Internal cavity means a natural cavity, for example an anal and/or vaginal cavity, or an artificial cavity fashioned by a surgeon.

Hereinafter in the description, use will be made of the terms "distal" and "proximal". In this context, such terms mean relative to the user; therefore, the term "proximal" means turned toward the "rear" parts of the device, farther from the patient, whilst the term "distal" means at the "front" parts, closer to the patient.

The proctoscope 1 comprises a dilator body 2, having a longitudinal axis of extension "X" and internally hollow so as to define an internal volume "V". The internal volume "V" is accessible from a front opening 3, with a substantially circular edge and preferably centred on the axis "X", and is further accessible from the rear through a rear opening 4, as may be seen in FIG. 1.

Figure 1:
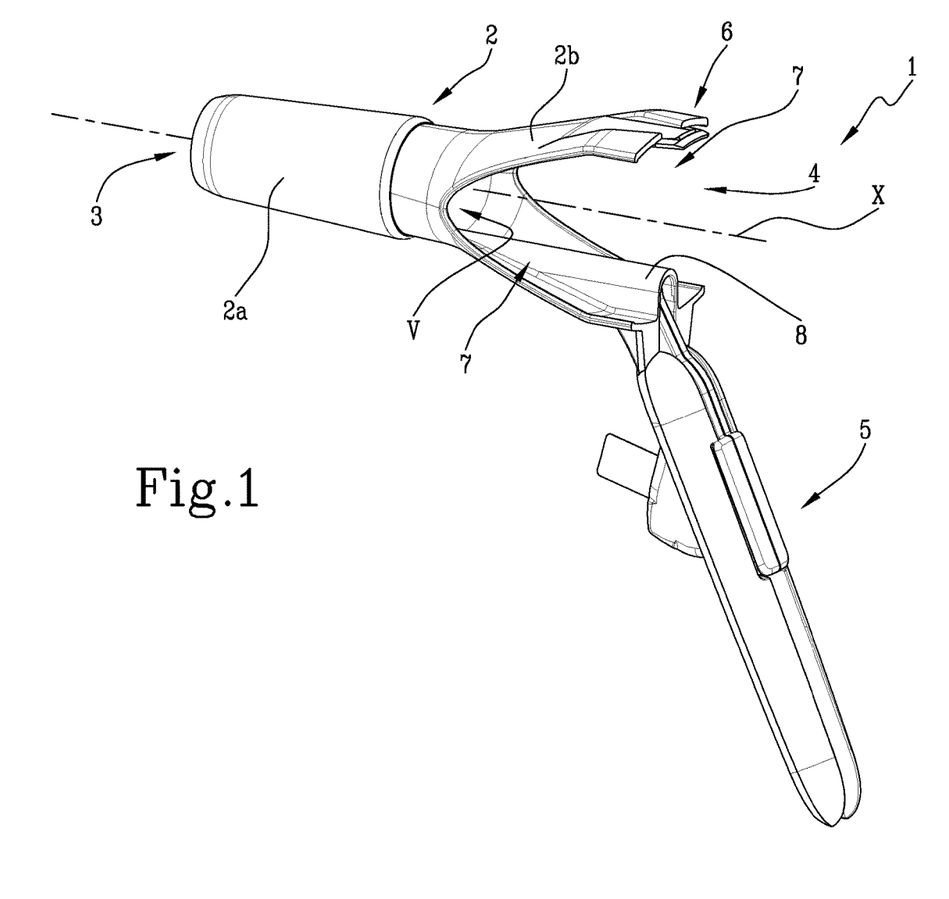
FIG. 1 shows a view of a proctoscope according to the present invention.
Figure 2:
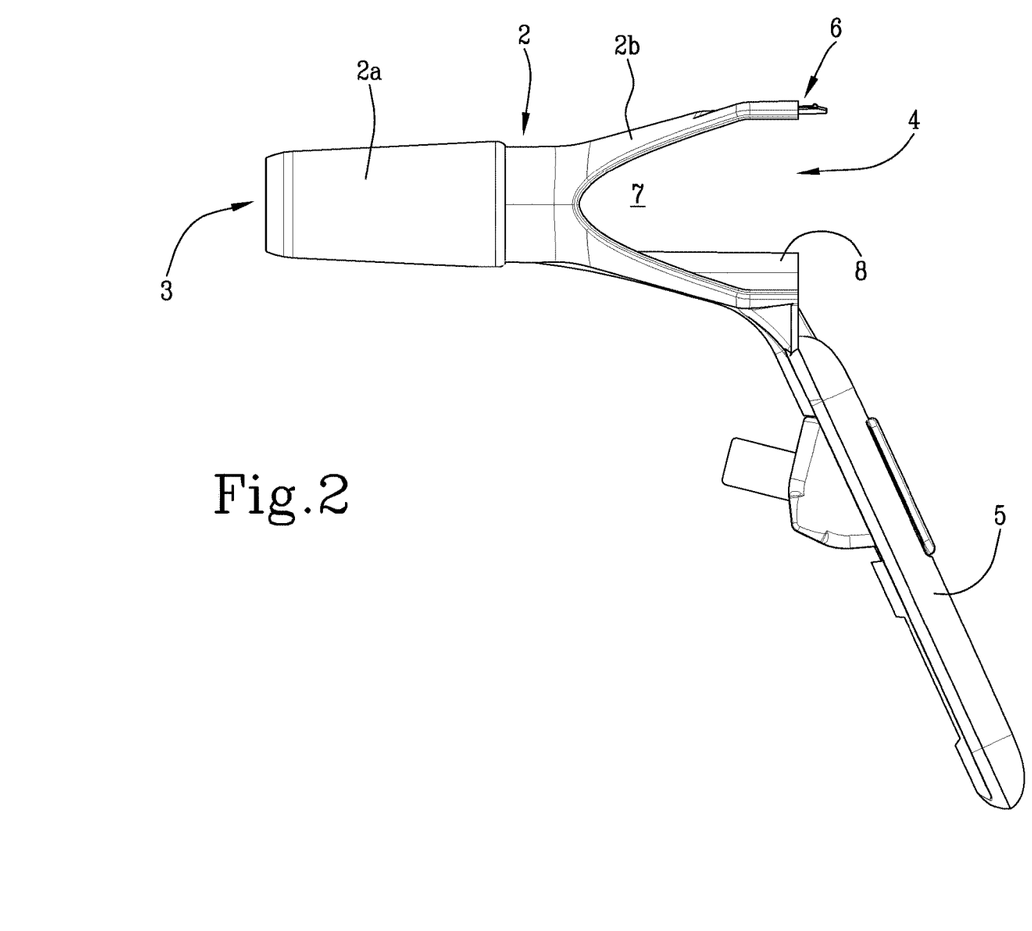
FIG. 2 shows a side view of the proctoscope of FIG. 1.

The dilator body 2 has a distal portion 2a, defining the aforesaid front opening 3 at the front thereof and having a substantially tubular shape (a cylindrical or slightly truncated cone shape or tapered towards the distal end thereof) for defining an zone of dilation of a cavity of a patient, and a proximal portion 2b extending from the distal portion 2a in a diverging fashion and defining said rear opening 4.

The proctoscope 1 further comprises at least one handle 5 applied to the dilator body 2, in particular to a lower part of the rear edge of the proximal portion 2b.

Said diverging proximal portion 2b has, in the embodiment illustrated in the appended FIGS. 1-6, an anchorage means 6 for an adaptor body 100 (which can be seen in FIGS. 5 and 6) and suitable for connecting a detection device 200 (which can be seen in FIG. 6), in particular a camera, to the proctoscope 1. The anchorage means 6 (for example of the snap-fit type) and the adaptor body 100 may have, in their essential features, a structure of a known type. With regard to the adaptor body 100, a particular feature according to the invention is that it has two opposing axial protrusions 101 configured to engage with corresponding regions of the diverging proximal portion 2b of the dilator body 2, in particular in proximity to the handle 5 and a region opposite the longitudinal axis of extension "X", as may be seen in FIGS. 5 and 6.

Figure 7:
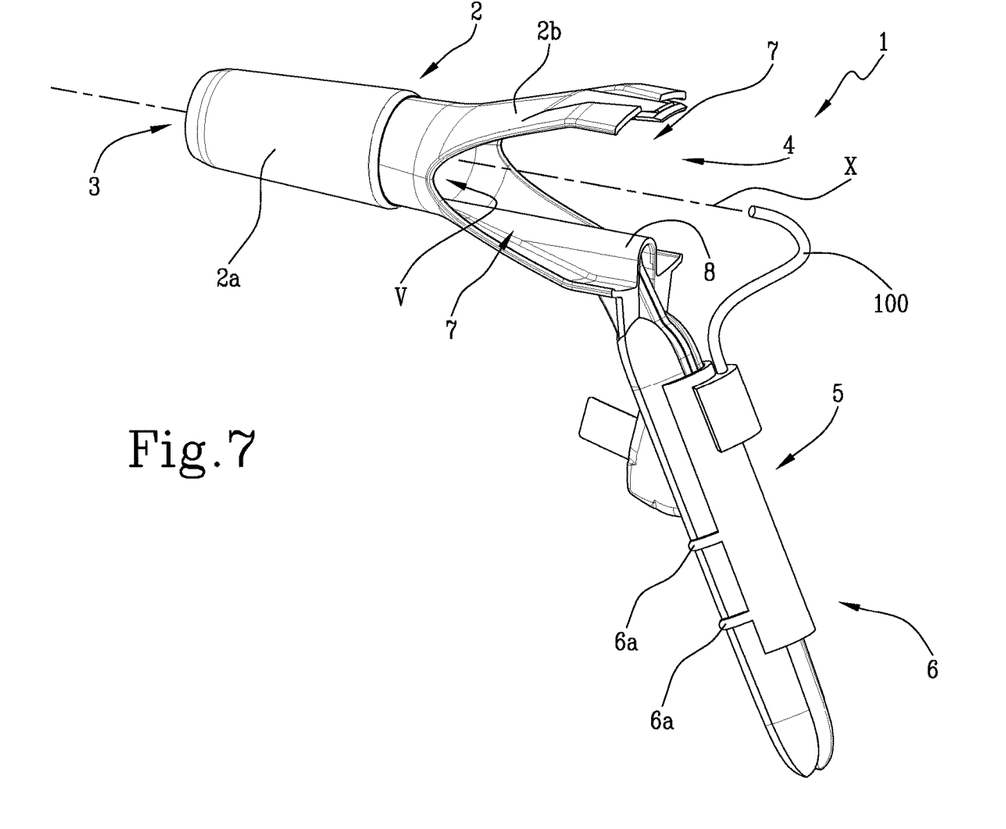
FIG. 7 shows a view of a proctoscope in a second embodiment.

In a further variant illustrated in FIG. 7, the aforesaid anchorage means 6 is connected to the at least one handle 5 and comprises coupling protrusions 6a in the lower part and a curved adaptor body 100 in the upper part, the adaptor body 100 being suitable for supporting a detection device 200, in particular a camera.

Figure 5:
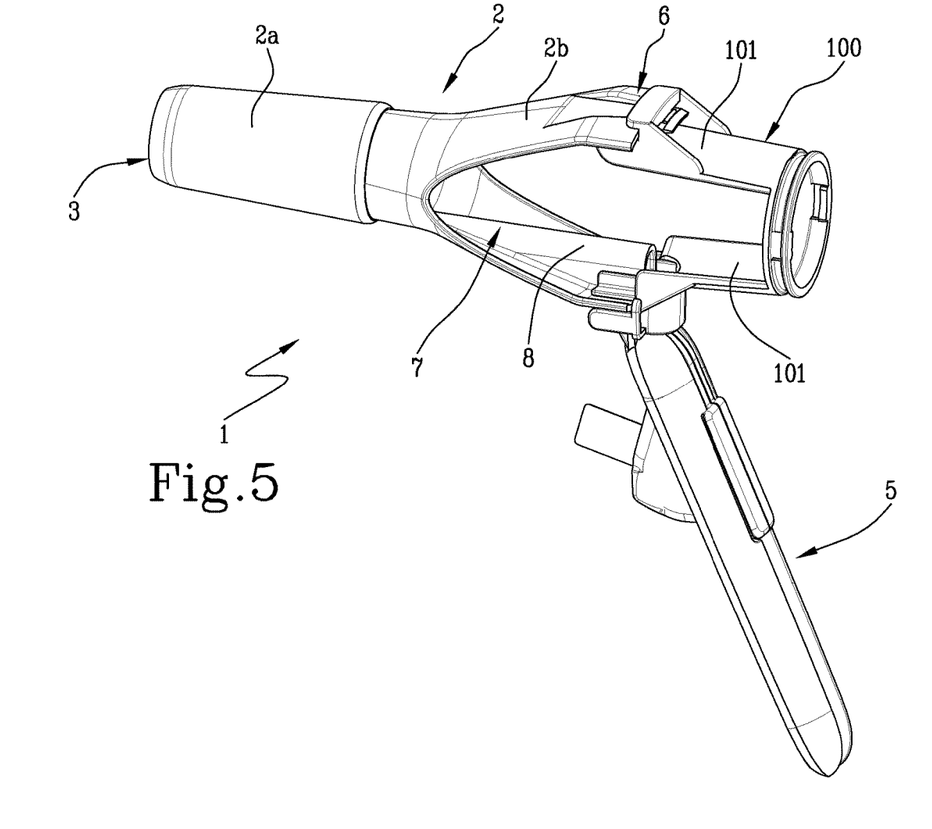
FIG. 5 shows a view of the proctoscope of FIG. 1 connected to an adaptor body for a camera.
Figure 6:
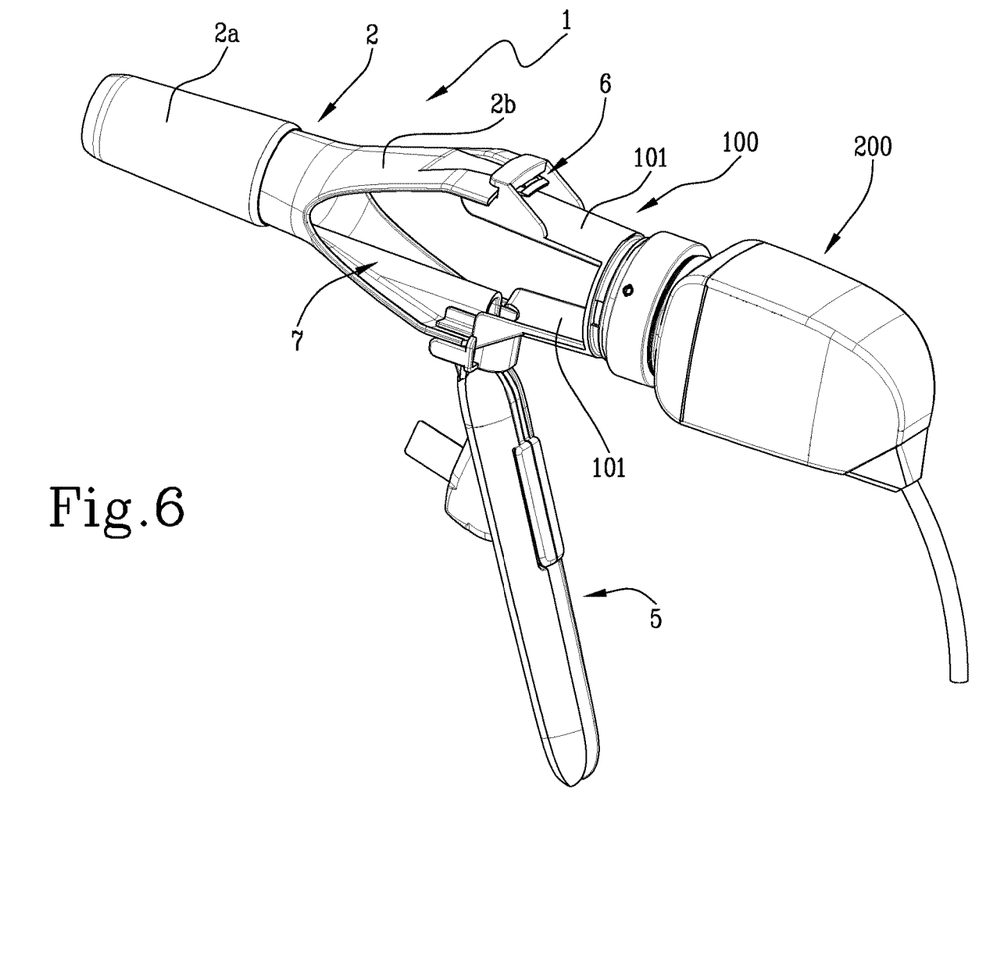
FIG. 6 shows a view of the proctoscope of FIG. 1 connected to an adaptor body for a camera and to a corresponding camera.

Advantageously, the dilator body 2 has, on the diverging proximal portion 2b, two auxiliary access openings 7 configured to enable the insertion of a means (not illustrated) for operating in the internal volume "V" through one or both of the auxiliary openings, also in a configuration wherein the proctoscope 1 is associated with the adaptor body 100 (FIGS. 5 and 6).

Preferably, the two auxiliary openings 7 are identical and define a symmetrical conformation of the proctoscope 1 (in particular relative to a vertical midplane in the view of FIG. 1).

Preferably, each auxiliary opening 7 has a conformation of diverging away from the distal portion 2a of the dilator body 2, in particular with a "U" or "V" shape with the concavity facing rearwards.

This diverging conformation of the auxiliary portion 7 is devoid of undercuts, since the auxiliary opening 7 is configured to fittingly receive a corresponding complementary lobe of an introducer body 300 (FIG. 3-4) by reciprocal translation along the longitudinal axis of extension "X".

Preferably, each auxiliary opening 7 extends along an entire axial extension of the diverging proximal portion 2b of the dilator body 2 along the longitudinal axis of extension "X".

Preferably, moreover, each auxiliary opening 7 extends only on the diverging proximal portion 2b, but not on the distal portion 2a of the dilator body 2.

Each auxiliary opening 7 extends to the rear edge of the diverging proximal portion 2b of the dilator body 2, thus defining a respective zone of perimetral interruption of the proximal portion 2b. The presence of two auxiliary openings 7 thus defines, in the embodiment illustrated in FIGS. 1-6, a subdivision of the diverging proximal portion 2a of the dilator body 2 into two portions, an upper one and a lower one (the latter connected to the handle 5), each associated with a respective part of the anchorage means 6.

The region of the diverging proximal portion 2b positioned between the two auxiliary openings 7 and opposite the handle 5 has a flattened shape, i.e. one having a radius of curvature greater than the distance from the longitudinal axis of extension "X" (the reason for this will be clarified below).

Preferably, each auxiliary opening 7 is angularly positioned, about the longitudinal axis of extension "X", at 90° relative to the handle 5.

Again making reference to the variant in FIGS. 1-6, the anchorage means 6 is angularly positioned, about the longitudinal axis of extension, substantially at 90° relative to the auxiliary openings 7.

In a preferred embodiment, as shown in the figures, the proctoscope 1 further comprises a light guide 8, in the form of a relief inside the dilator body 2, which extends along the longitudinal axis of extension "X" in a distal direction from the handle 5.

Figure 3:
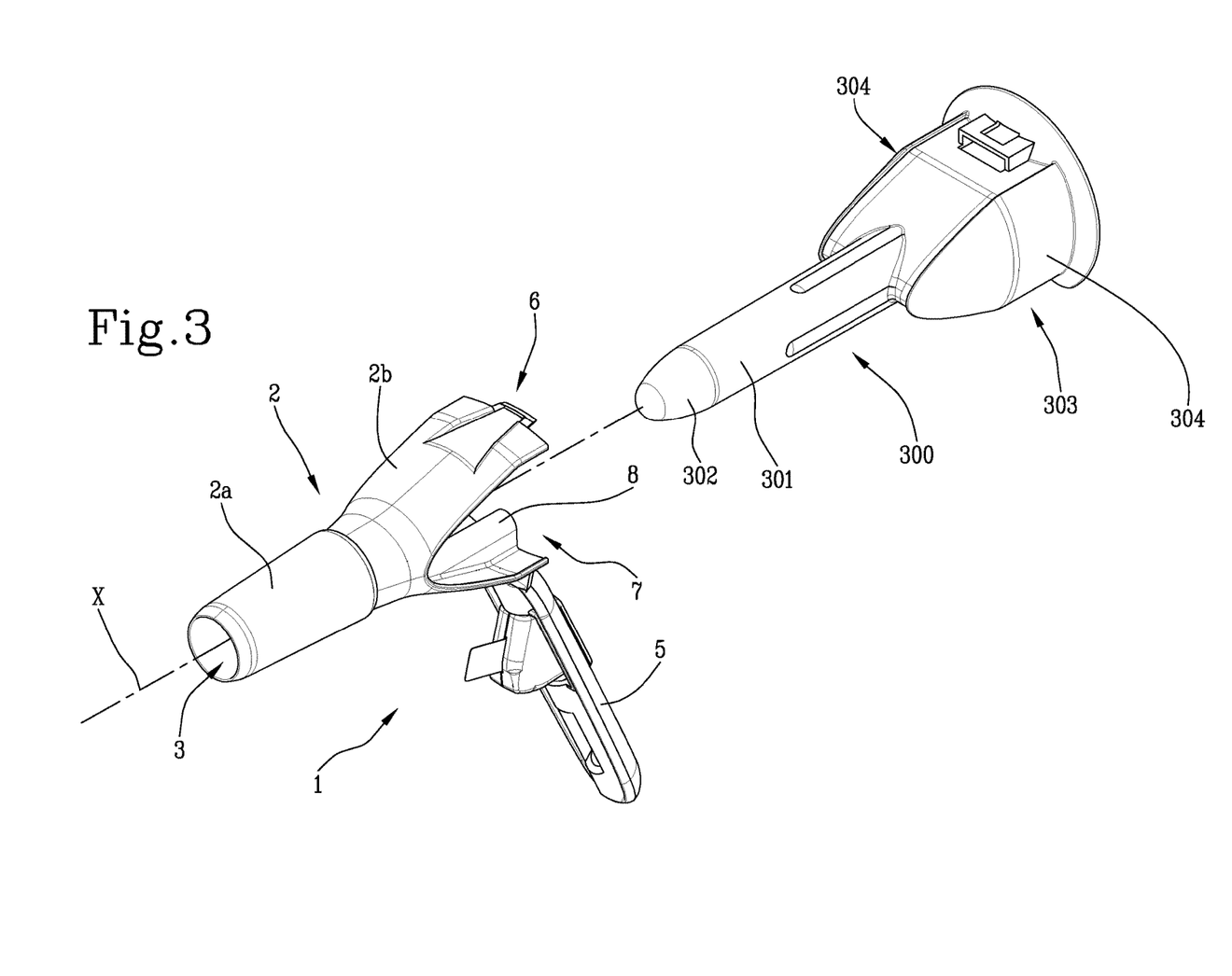
FIGS. 3 and 4 represent two views of the proctoscope of FIG. 1 together with an introducer body, in a configuration in which they are ready to be coupled and in a coupled configuration, respectively.
Figure 4:
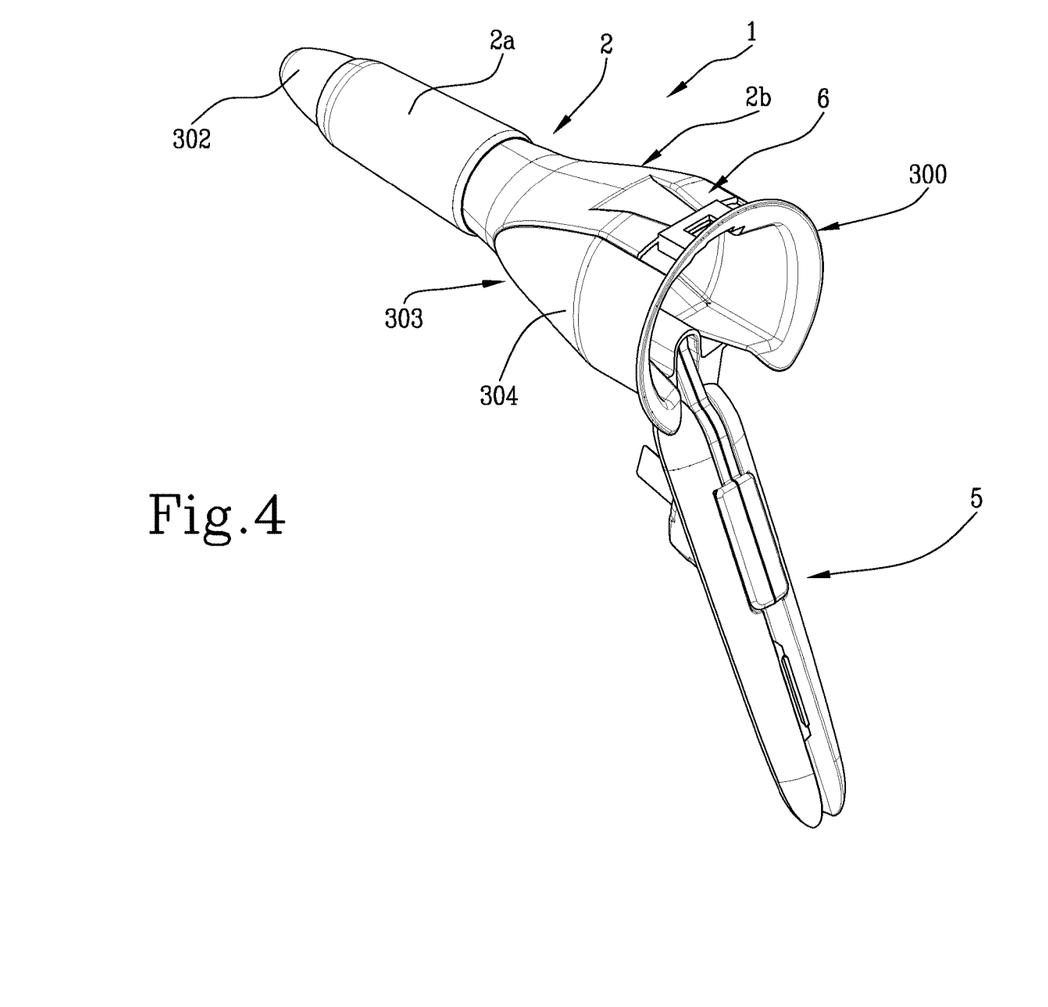

FIGS. 3 and 4 show in detail the proctoscope 1 in association with a respective introducer body 300, respectively in a configuration in which they are ready to be coupled and in a coupled configuration.

The introducer body 300 has a distal portion 301 of a cylindrical or tubular shape, configured for insertion into the distal portion 2a of the dilator body 2 and having a rounded or pointed end 302 intended to come out of the front opening 3 of the proctoscope 1.

The introducer body 300 further has a proximal portion 303 with a larger cross section, configured to be coupled in a complementary manner with the proximal portion 2b of the dilator body and having, in particular, two opposite lobes 304, each configured to be fittingly inserted into a corresponding auxiliary opening 7 in such a manner that, in a configuration of coupling between the dilator body 2 and introducer body 300, the proximal portion 2a of the dilator body 2 and the proximal portion 301 of the introducer body 300 define an outer continuous surface devoid of irregularities or steps between the two proximal portions 2a, 301.

In order to achieve this, the rear opening 4 and the lateral auxiliary openings 7 define a single recess with the concavity facing rearward and configured to receive, in a complementary manner, the proximal portion 301 of the introducer body 300.

Preferably, moreover, said continuous outer surface has, in a section transversal to the longitudinal axis of extension "X", an elliptical shape that is flattened in the horizontal direction. This explains why, as said previously, the region of the diverging proximal portion 2b positioned between the two auxiliary openings 7 and opposite the handle 5 has a "flattened" shape.

In the illustrated embodiment, the introducer body 300 is stably couplable to the proctoscope 1 via the anchorage means 6, which is thus configured for connection to both the adaptor body 100 and the introducer body 300.

FIGS. 5 and 6 show the proctoscope 1 associated with the adaptor body 100 (FIG. 5) and also with a camera 200 (FIG. 6). In said figures it may be noted that the presence of the adaptor body 100 coupled to the proximal portion 2b of the dilator body 2 does not interfere with the accessibility to the internal volume "V" through the lateral auxiliary openings 7, which are moreover delimited at the front, top and bottom by the diverging profile of the proximal portion 2b and at the rear by the profile the adaptor body 100.

FIG. 7 illustrates a variant of the proctoscope 1, in which the adaptor body 100 supports a camera 200 suitable for detecting the internal volume of the proctoscope itself.

In this variant the camera 200 does not particularly interfere with the inside of the dilator body 2, but the auxiliary openings 7 allow the surgeon a greater freedom of movement of any surgical instrument inserted through the rear opening 4 and coming out of the front opening 3.

A method for carrying out an investigation on a cavity of a patient using the above-described proctoscope comprises the following steps:
- introducing at least partially the dilator body 2 inside a cavity of the patient;
- applying a detection device 200, in particular a camera, to the diverging proximal portion 2b of the dilator body 2 by interposition of an adaptor body 100 coupled to the anchorage means 6, so that the camera 200 is facing the internal volume of the dilator body "V" (FIG. 6) and is capable of taking images of a portion of the internal cavity of the patient through the front opening 3 of the dilator body 2;
- turning on the camera 200 so as to take images of said portion of the internal cavity;
- inserting at least one surgical instrument, for example an electrosurgical unit, into the internal volume "V" of the dilator body 2 through at least one of the auxiliary openings 7 while the dilator body 2 is inserted in the cavity of the patient and while the camera 200 is turned on and mounted on the proctoscope 1 via the adaptor body 100;
- carrying out a surgical treatment of a portion of mucosa of the anal canal by means of the surgical instrument inserted into the internal volume "V" of the dilator body 2 through the auxiliary opening 7.

The embodiment illustrated and described above has a pair of auxiliary lateral openings 7 opposite each other. However, the invention can also be equally applied to an embodiment (not illustrated) in which it has only one of the two auxiliary openings 7, either on the left side or the right side, in a configuration of the proctoscope with the handle turned downwards.

The present invention achieves the proposed object, overcoming the aforementioned drawbacks in the prior art.

Thanks to the lateral openings, in fact, the proctoscope makes it possible to operate with surgical instruments even in the presence of the camera coupled at the rear with the proctoscope, thus increasing the flexibility of use of the proctoscope both from a diagnostic standpoint and a surgical standpoint.

The invention claimed is:

1. A proctoscope, comprising a dilator body, having a longitudinal axis of extension and internally hollow so as to define an internal volume, and at least one handle applied to said dilator body, wherein the dilator body has a distal portion, having a substantially tubular shape and defining a zone of dilation of an internal cavity of a patient, and a proximal portion extending from the distal portion in a diverging fashion and defining a rear opening for accessing said internal volume, wherein said distal portion of the dilator body has at least one front opening to enable access to the patient's mucosa or tissue from said internal volume, and wherein said diverging proximal portion, or, alternatively, said at least one handle, has an anchorage means;

said proctoscope further comprising an adaptor body stably and removably coupled to said anchorage means and a detection device, stably applied to the adaptor body on the opposite side relative to said diverging proximal portion of the dilator body such as to detect the internal volume of proctoscope;

in which said dilator body has, on said diverging proximal portion, at least one auxiliary access opening configured to enable the insertion of a means for operating in the internal volume through said auxiliary opening, and wherein said at least one auxiliary opening is delimited in part by said dilator body and in part by said adaptor body and/or detection device;

wherein said at least one auxiliary opening is angularly positioned, about said longitudinal axis of extension, at 90° relative to said handle.

2. The proctoscope according to claim 1, wherein said auxiliary opening has a conformation of diverging away from the distal portion.

3. The proctoscope according to claim 1, wherein said auxiliary opening extends along an entire axial extension of the diverging proximal portion along said longitudinal axis of extension.

4. The proctoscope according to claim 1, wherein said auxiliary opening extends solely on the diverging proximal portion but not on the distal portion.

5. The proctoscope according to claim 1, wherein said auxiliary opening extends to a rear edge of the diverging proximal portion.

6. The proctoscope according to claim 1, wherein said anchorage means, when placed on the diverging proximal portion, is angularly positioned, about said longitudinal axis of extension, at 90° relative to said at least one auxiliary opening.

7. The proctoscope according to claim 1, wherein said front opening is positioned on said front end of the distal portion and extends around said longitudinal axis of extension.

8. The proctoscope according to claim 1, further comprising a light guide, in the form of a relief inside said dilator body extending along said longitudinal axis of extension in a distal direction from the handle.

9. The proctoscope according to claim 1, further comprising an introducer body having a distal portion insertable in the distal portion of the dilator body and a proximal portion having a shape complementary to said proximal portion of the dilator body so that, in a configuration of coupling between the dilator body and the introducer body, the proximal portion of the dilator body and the proximal portion of the introducer body define an outer continuous surface devoid of irregularities or steps between the two proximal portions.

10. The proctoscope according to claim 9, wherein, in said coupling configuration the two mutually coupled proximal portions define an outer profile of an elliptical shape in a section transversal to said longitudinal axis of extension.

11. The proctoscope according to claim 1, wherein said detection device is a camera.

12. A method for carrying out an investigation on an internal cavity of a patient, comprising the steps of:
providing a proctoscope according to claim 1;
introducing at least partially the dilator body inside the internal cavity of the patient;
applying a detection device to the dilator body by interposition of an adaptor body coupled to said anchorage means, so that said detection device is facing the internal volume of the dilator body and is capable of taking images of a portion of the internal cavity of the patient through said front opening of the dilator body;
turning on said detection device so as to take images of said portion;
inserting at least one surgical instrument into the internal volume of the dilator body through said at least one auxiliary opening while the dilator body is inserted in the internal cavity of the patient and while said detection device is turned on;
carrying out a surgical treatment inside the internal cavity of the patient by means of said surgical instrument inserted in the internal volume of the dilator body through said at least one auxiliary opening.

13. A method according to claim 12, wherein the step of applying a detection device is realized by applying a camera.

14. A proctoscope, comprising a dilator body, having a longitudinal axis of extension and internally hollow so as to define an internal volume, and at least one handle applied to said dilator body, wherein the dilator body has a distal portion, having a substantially tubular shape and defining a zone of dilation of an internal cavity of a patient, and a proximal portion extending from the distal portion in a diverging fashion and defining a rear opening for accessing said internal volume, wherein said distal portion of the dilator body has at least one front opening to enable access to the patient's mucosa or tissue from said internal volume, and wherein said diverging proximal portion, or, alternatively, said at least one handle, has an anchorage means;

said proctoscope further comprising an adaptor body stably and removably coupled to said anchorage means and a detection device, stably applied to the adaptor body on the opposite side relative to said diverging proximal portion of the dilator body such as to detect the internal volume of proctoscope;

in which said dilator body has, on said diverging proximal portion, at least one auxiliary access opening configured to enable the insertion of a means for operating in the internal volume through said auxiliary opening, and wherein said at least one auxiliary opening is delimited in part by said dilator body and in part by said adaptor body and/or detection device;

wherein said dilator body has, on said diverging proximal portion, two auxiliary openings of an identical shape set in a reciprocally opposite position relative to said longitudinal axis of extension.

15. The proctoscope according to claim 14, wherein said diverging proximal portion, in a region thereof positioned between the two auxiliary openings and opposite the handle, has a flattened shape and is provided with at least a part of said anchorage means.

* * * * *